US00PP35225P3

(12) United States Plant Patent
Walsh et al.

(10) Patent No.: US PP35,225 P3
(45) Date of Patent: Jun. 20, 2023

(54) APPLE TREE NAMED 'MD-TAP1'

(50) Latin Name: *Malus domestica*
Varietal Denomination: MD-TAP1 (formely—'WYE 190')

(71) Applicant: University of Maryland, College Park, College Park, MD (US)

(72) Inventors: Christopher S. Walsh, University Park, MD (US); Julia M. Harshman, Ventura, CA (US); Kathleen W. Hunt, Seabrook, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 17/663,313

(22) Filed: May 13, 2022

(65) Prior Publication Data

US 2022/0369525 P1 Nov. 17, 2022

Related U.S. Application Data

(60) Provisional application No. 63/201,847, filed on May 14, 2021.

(51) Int. Cl.
*A01H 5/08* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./156, 161, 175, 172
See application file for complete search history.

(56) References Cited

U.S. PATENT DOCUMENTS

PP3,637 P 10/1974 McKenzie
PP4,382 P 2/1979 Wijcik
PP9,392 P 12/1995 Crosby et al.

*Primary Examiner* — Karen M Redden
(74) *Attorney, Agent, or Firm* — McKee, Voorhees & Sease, PLC

(57) ABSTRACT

A new and distinctive variety of *Malus domestica* apple tree named 'MD-TAP1' is distinguished by its attractive tree architecture, reduced need for hand pruning and training, and fruit which is harvested six weeks earlier than its seed parent.

6 Drawing Sheets

Latin name: *Malus domestica.*
Varietal denomination: MD-TAP1 (formerly—'WYE 190').

BACKGROUND

The invention refers to a new plant variety of apple tree (*Malus domestica*) named 'MD-TAP1'. The new variety is distinguished by its attractive tree architecture, reduced need for hand pruning and training, and fruit which is harvested six weeks earlier than its seed parent. 'MD-TAP1' originated as a single seedling from an open pollination of the seed parent 'Co-op 38' (also known as Goldrush, U.S. Plant Pat. No. 9,392). The seed parent tree was grown in an isolated block of research seedlings. Those research seedlings provided the putative pollen parent tree. That pollen parent was an unpatented apple tree, previously derived from an open pollination of the columnar apple tree, 'McIntosh Wijcik' (U.S. Plant Pat. No. 4,382) by 'Gala' (U.S. Plant Pat. No. 3,637, expired). Therefore, 'MD-TAP1' is presumed to have the pedigree 'Co-op 38' x ('McIntosh Wijcik' x 'Gala').

The original 'MD-TAP1' seed was removed from fruit produced in 2002. That seed was germinated, grown in a greenhouse, and then transplanted in the field in Queenstown, Queen Anne's County, Md. in 2003. This original tree was observed to annually produce large, good-quality fruit. In 2015 budwood was taken from this original 'MD-TAP1' tree and bench-grafted onto clonal rootstocks of 'M.111' (unpatented) purchased in Ephrata, Wash. Grafted trees were planted in Keedysville, Washington County, Md. Grafted trees were also planted in Queenstown, Queen Anne's County, Md. where they could be compared with the original 'MD-TAP1' tree. Grafted trees from both locations were observed from 2016 until 2021. During that time, the leaves, flowers, fruit, shoots and trunk were found to be stable and essentially similar to those of the original seedling tree.

BRIEF SUMMARY

The 'MD-TAP1' variety exhibits exceptional tree architecture. With its mesotonic growth habit, wide-angle branches, and shoot di-morphy leading to a spur-type habit, the tree canopy is open. Most fruiting shoots (spurs) receive full sunlight. Upright branches are not rigid and arch downward with a typical crop load. Buds from the original seedling tree grown in Queen Anne's County, Md. were vegetatively propagated by grafting on 'M.111' rootstocks and planted at research locations in Queen Anne's County and Washington County, Md. The original seedling tree and the grafted trees on 'M.111' rootstocks were precocious; they began to flower and fruit in their fourth growing seasons. The fruit size of 'MD-TAP1' is large and somewhat similar to that of its seed parent 'Co-op 38', but matures approximately six weeks earlier than that variety. It is a mid-to-late-September apple when grown in Washington County, Md. In addition to maturing much earlier than 'Co-op 38', the fruit does not appear to be susceptible to the preharvest cracking that occurs when 'Co-op 38' fruit are produced in Maryland. These attributes coupled with its large fruit and annual production appear to make 'MD-TAP1' well-suited for sustainable, organic, and home-grounds fruit planting.

BRIEF DESCRIPTION OF THE DRAWINGS

This new apple variety 'MD-TAP1' is illustrated by the accompanying photographic drawings of the plant growing at the research farms in Washington County, Md. and Queen Anne's County, Md. These drawings show the tree, fruit, and leaves using color photography. Colors shown are approximate as they can depend on horticultural practices, weather conditions, and management strategies. Consequently, the color characteristics of this new variety should be determined from the observations described herein rather than these drawings.

Figure 1:
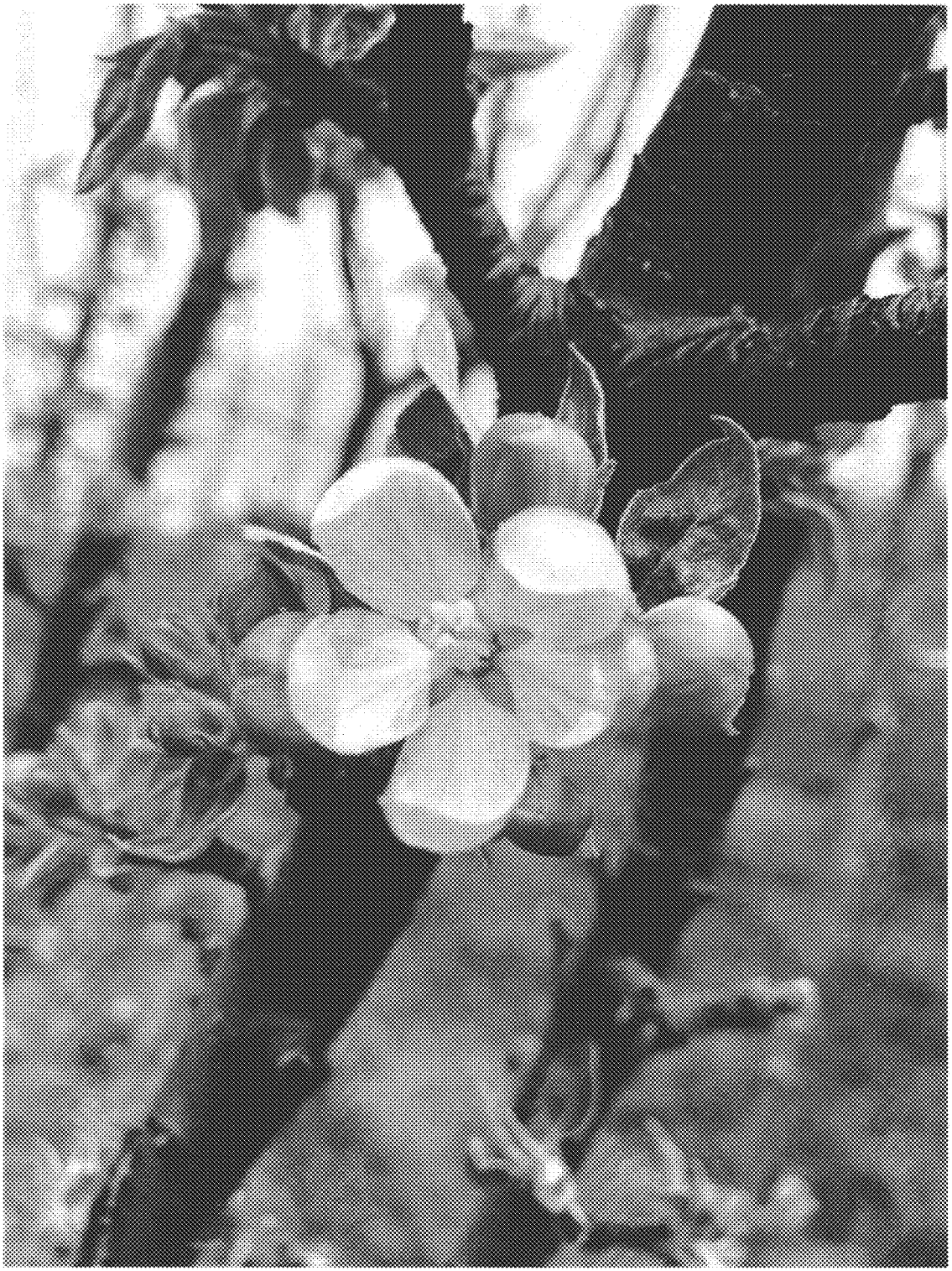
FIG. 1 is a color photograph taken on Apr. 13, 2022 of 'MD-TAP1' apple flower and unopened flower buds.
Figure 2:
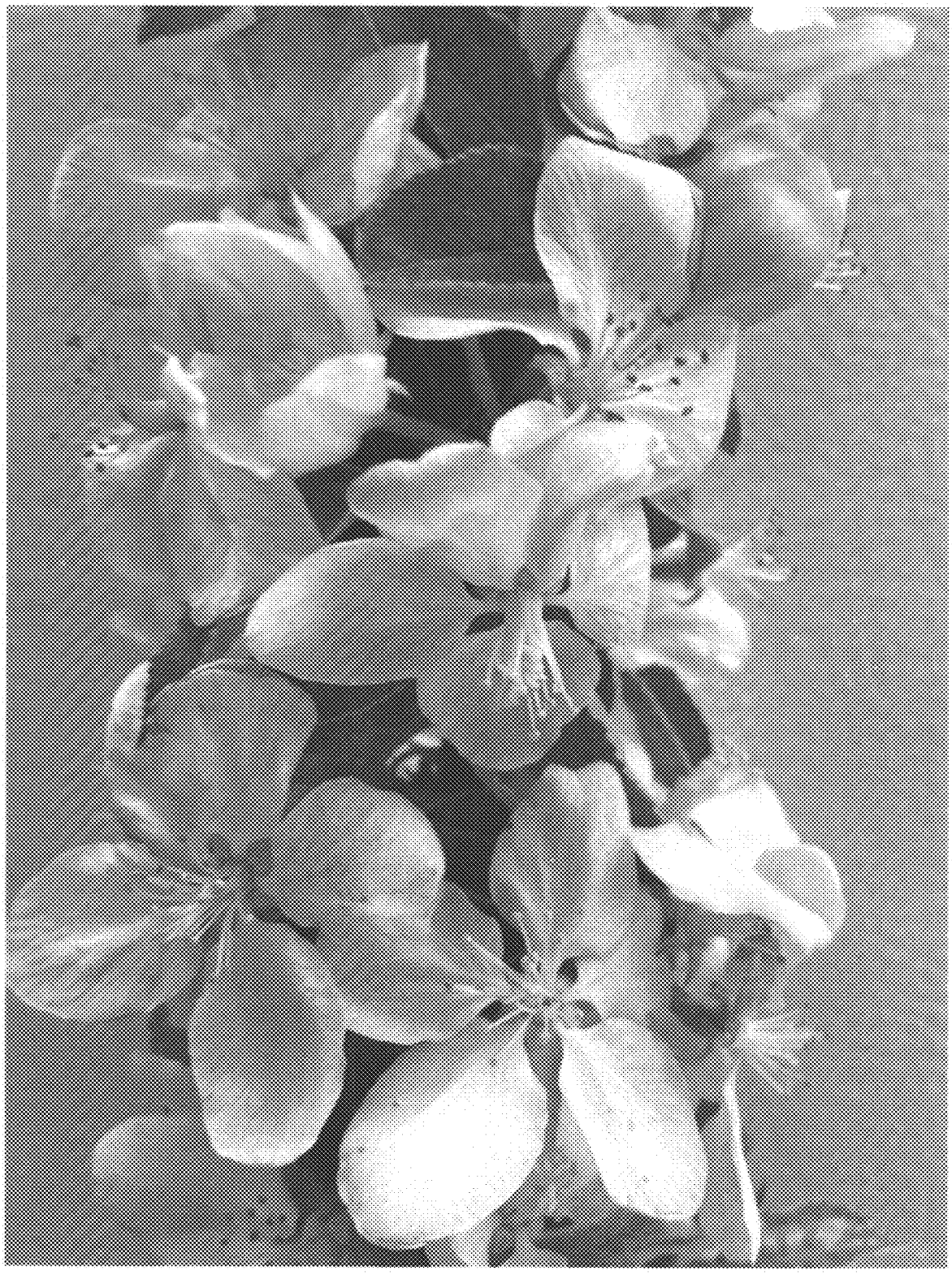
FIG. 2 is a color photograph taken on Apr. 28, 2022 of 'MD-TAP1' apple flowers and leaves on one-year old shoot that developed in the 2021 growing season
Figure 3:
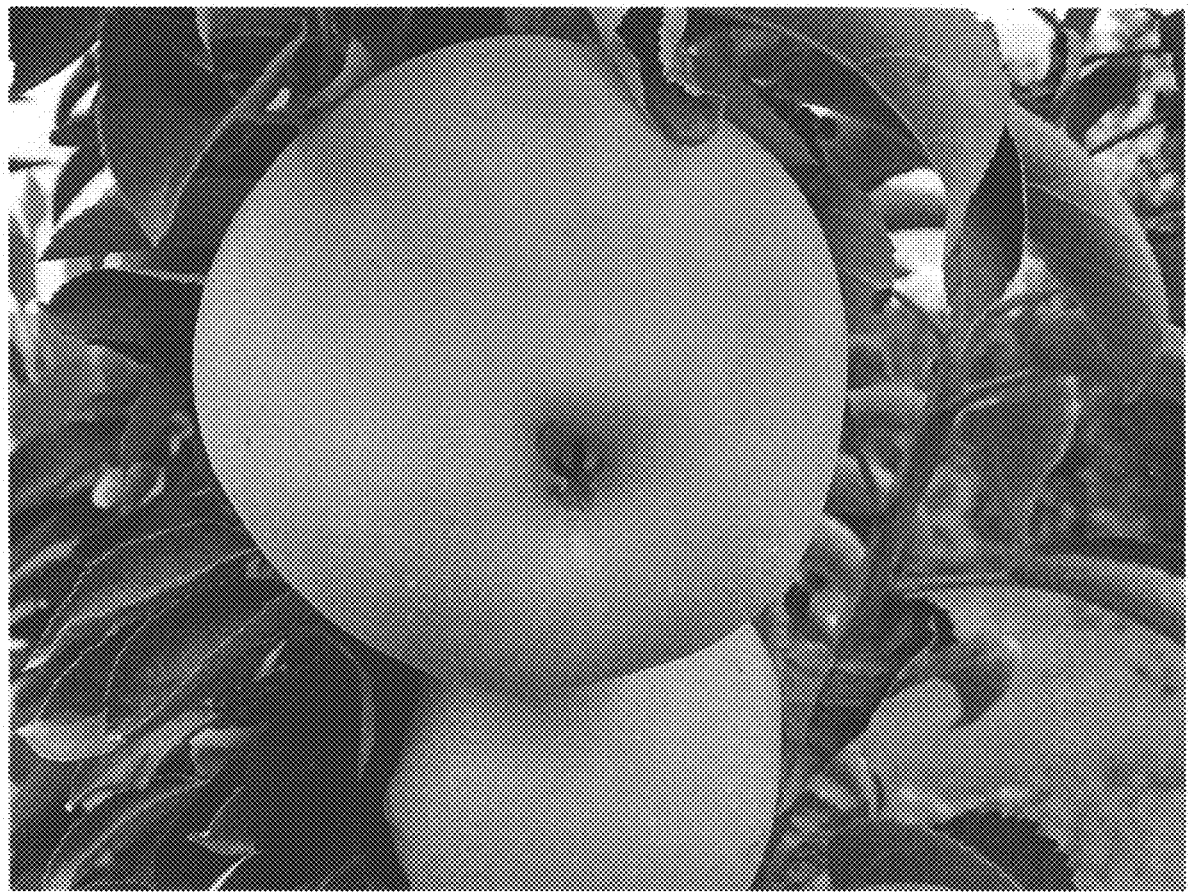
FIG. 3 is a color photograph taken on Sep. 9, 2019 of 'MD-TAP1' apple fruit and leaves prior to harvest.
Figure 4:
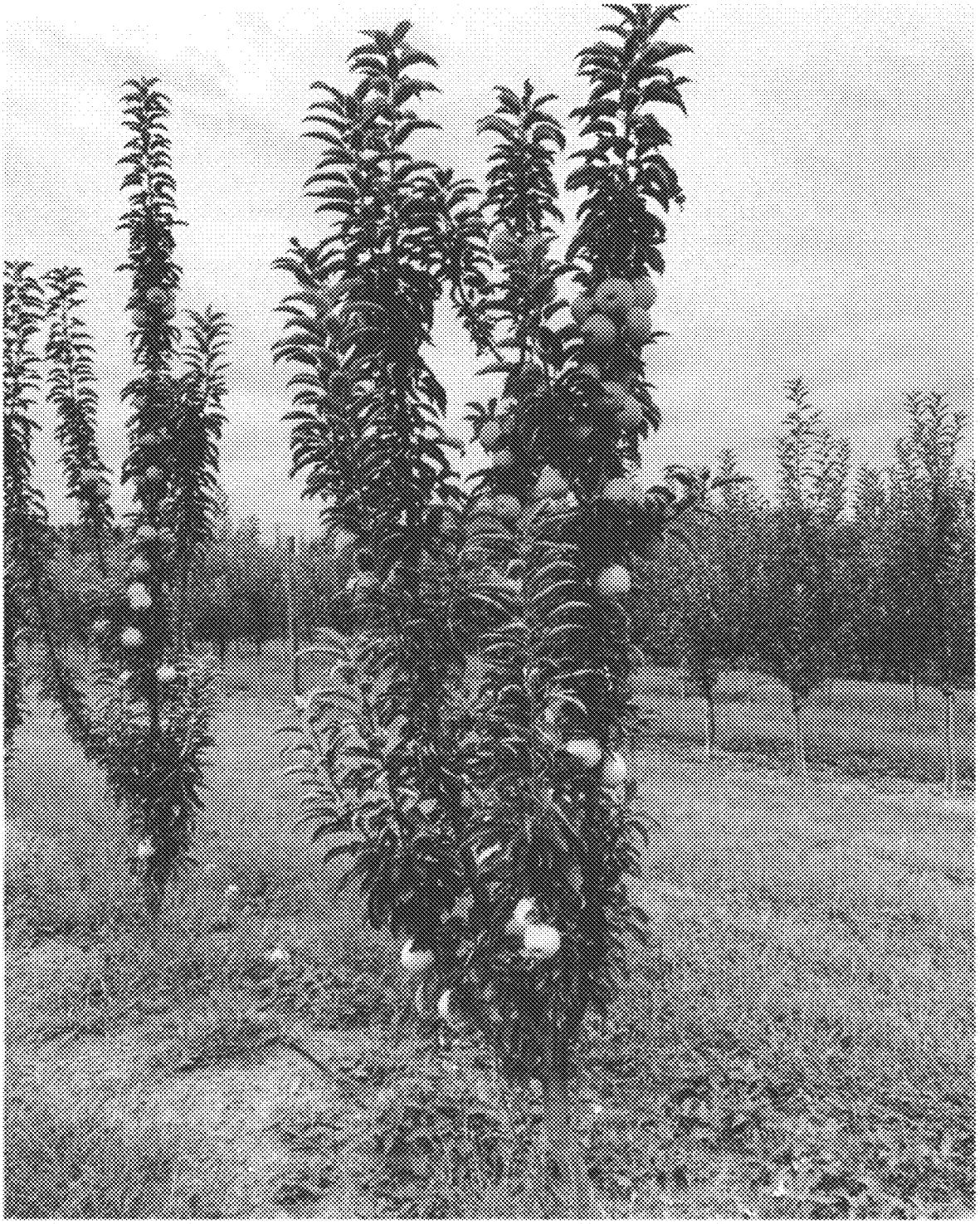
FIG. 4 is a color photograph taken on Sep. 9, 2019 of two 'MD-TAP1' apple trees budded onto 'M.111' rootstock showing early fruit yield and size.
Figure 5:
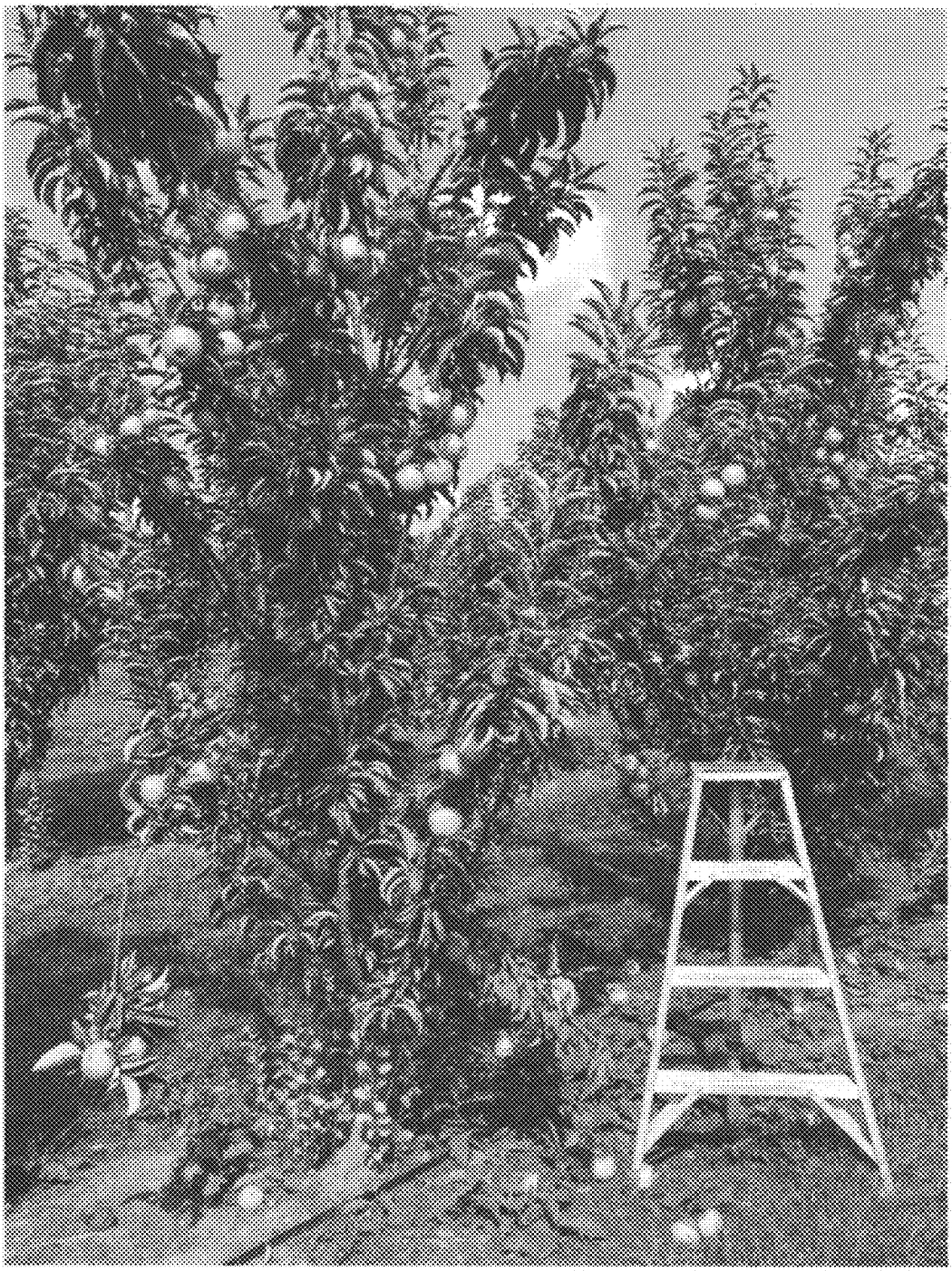
FIG. 5 is a color photograph taken on Sep. 16, 2020 of two 'MD-TAP1' apple trees and a step ladder showing the tree branches bent down with the weight of ripening fruit.
Figure 6:
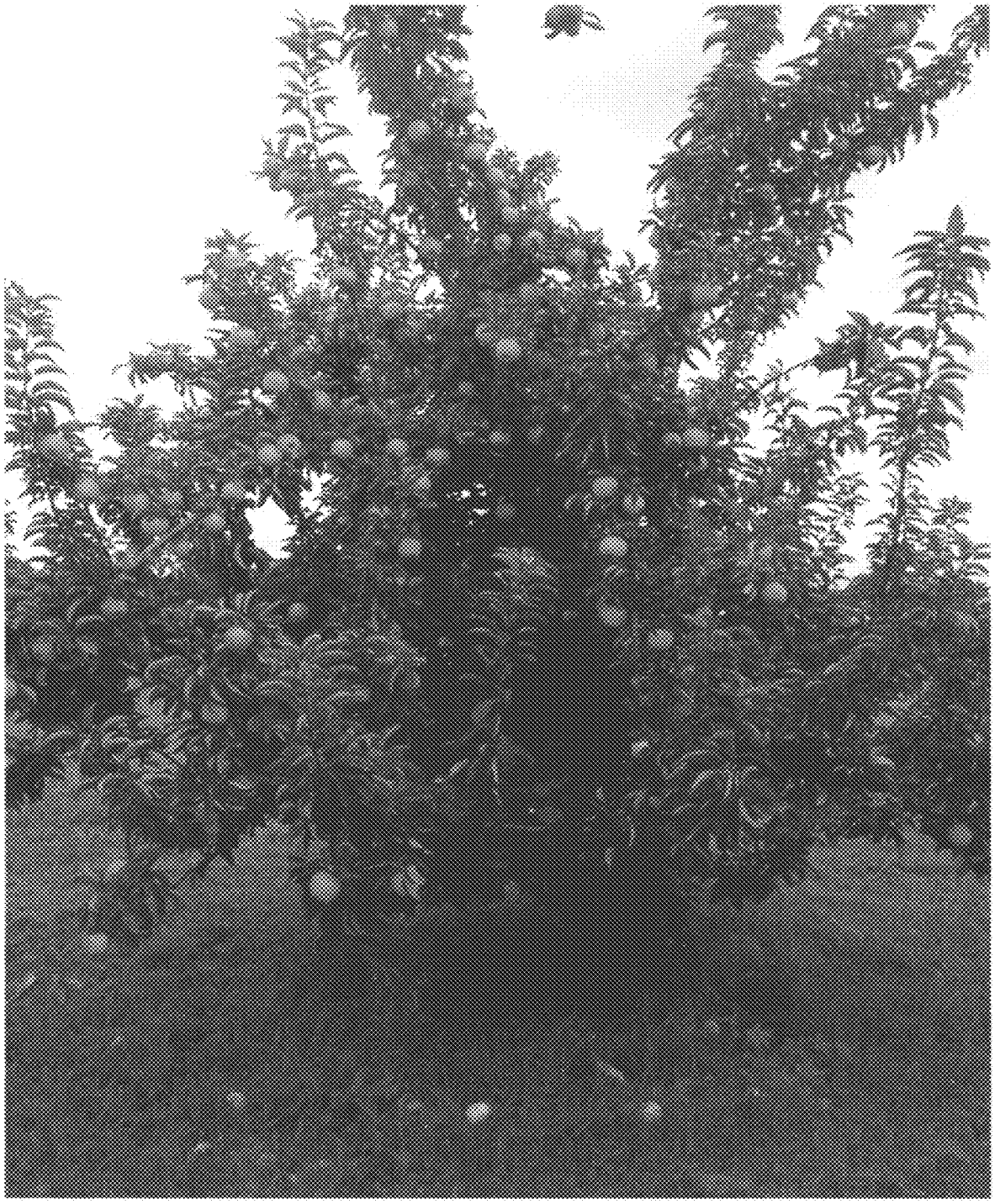
FIG. 6 is a color photograph taken on Sep. 24, 2014 of the original unpruned 'MD-TAP1' seedling apple tree showing its natural tree architecture.

DETAILED BOTANICAL DESCRIPTION.

The following detailed description of 'MD-TAP1' tree was made on trees budded onto 'M.111' rootstocks grown at Keedysville, Md. in Washington County. Measurements of the fruit were taken in 2020, and the measurements of the flowers were taken in 2021. All color references are taken from The Royal Horticultural Society (R.H.S.) Colour Chart, 5$^{th}$ Edition.

Scientific name: *Malus* x *domestica* Borkh.

Parentage:

*Seed parent*.—'Co-op 38'.

*Pollen parent*.—Unnamed seedling apple tree derived from a 1991 'McIntosh Wijcik' x 'Gala' cross previously created by one of the co- inventors, C S Walsh, in Washington County, Md.

Tree:

*Vigor*.—Moderate.

*Plant hardiness zone*.—Growth of plants has been observed in USDA Zone 6b.

*Dormant flower bud cold tolerance*.—At least −5° F. (−17.8° C.).

*Overall shape*.—Conical.

*Height*.—14.1 feet (4.3 meters).

*Width*.—8.7 feet (2.65 meters).

Trunk and branches:

*Trunk bark color*.—Greyed-brown (RHS 199C).

*Primary branches*.—Greyed-green (RHS 197B to Greyed-brown (RHS 199B).

*Branch angle*.—Ranges between 45 and 90° from the trunk.

*Lenticels*.—8 round to oval lenticels per cm$^2$.

*Terminal shoots*.—62 cm in length and 11 mm diameter at the mid-point of the shoot.

*New growth bark*.—Greyed-orange (RHS 166A) at the basal internodes of the shoot, fading to Greyed-orange (RHS 165A) at the mid- and sub-apical internodes of the shoot.

*Internode, one-year-old shoot*.—1.8 cm in length and 9.2 mm in diameter.

Leaves:

*Texture*.—Upper surface smooth; lower surface slightly velvety.

*Length*.—Fully expanded mid-shoot leaf blades average 12.4 cm.

*Width*.—Fully expanded mid-shoot leaf blades average 8.5 cm.

*Apex*.—Acute; flexing downward.

*Venation*.—Pinnate.

*Margin*.—Serrated; about 4 teeth per cm.

*Petioles*.—3.5 cm in length and 2.8 mm in diameter with a color of Greyed-red (RHS 181A).

*Stipules*.—Two with an average length of 11 mm.

Leaf color:

*Upper leaf surface*.—Green (RHS 131A).

*Lower leaf surface*.—Green (RHS 133D).

*Vein*.—Green (RHS 129D).

Flowers:

*Arrangement*.—Intermediate.

*Size*.—Considered large; when fully expanded diameter ranged from 6.8 cm to 7.2 cm; the number of blossoms per bud is 4 to 6.

*Petals*.—5 ovate petals per flower; petal length ranges from 20 to 26 mm with an average of 24. Width ranges from 15 to 19 mm with an average of 17 mm. Petal margins are smooth; tip and base of attachment narrows to a stalk 2.9 mm wide and 2.9 mm in length.

*Petal color*.—Upper and lower surfaces are white (RHS NN155C). and were exposed prior to opening; surface has red-purple highlights (ranging from RHS N73A to N74C) to sometimes purple highlights (RHS 76B).

*Pistil*.—Typically 5 pistils per flower; length ranges from 10 to 15 mm with an average of 13 mm; Styles: 5 in number fused at half the distance to the basal end with the fused region covered with white pubescence. Yellow-green color (RHS 145A).

*Stigma*.—Round; Yellow-green (RHS 145B).

*Stamens*.—Number ranges from 18 to 21, typically 18; filament length ranges from 8 to 13 mm with an average of 11 mm. Filament color is Yellow-green (RHS 145C).

*Pollen*.—Color is Greyed-yellow (RHS 162C).

*Flower sepals*.—5 per blossom; deltoid shape with an acuminate tip and truncated base. Length ranges from 5 to 9 mm with an average of 7 mm; width ranges from 2 to 4 mm with an average of 3 mm.

*Flower calyx shape*.—Circular.

*Sepal color*.—Upper surface color is Green (RHS 142C) at the tip to Green (RHS 142D) at the point of attachment.

*Pedicel length*.—Length ranges from 8 to 9 mm with an average of 8.7 mm; color is Yellow-green (RHS 146C).

*Bloom season*.—Early-season. In 2021, bloom began on Apr. 13, 2021 and ended on Apr. 23, 2021 with full bloom on April 15 in the Washington County, Md. research orchard. In 2022, the time of first flowering was April 13.

Fruit:

*Size*.—Considered large with a normal crop load, produced annually without the need for hand or chemical thinning. Diameter measures 83.4 mm; weight increased from 190 g at the beginning of September to 249 g at the end of September 2020.

*Shape*.—Considered uniform, round-conical.

*Color*.—Ground color transitions from Yellow-green (RHS 151D) to Greyed-yellow (RHS 160B) at the end of harvest; A pale orange-red overcolor (RHS 34D) covers 5 to 20 percent of some fully-exposed fruit.

*General color effect*.—Light Orange-red (RHS 34D) over Greyed-yellow (RHS 160B) in ripe fruit.

*Skin*.—Medium thickness; no waxy bloom.

*Stem*.—Variable length, ranging from 8 mm to 30 mm with an average of 19 mm; 3.5 mm in diameter.

*Cavity*.—Flaring and smooth; sometimes russet.

*Eye basin*.—Width ranging from 22 to 26 mm, depending on fruit size; average depth is 14 mm.

*Size of eye*.—7.8 mm.

*Calyx*.—Calyx basin is flaring and smooth.

*Calyx tube*.—Crown-shaped; sepals persistent, reflexed and not touching; open.

*Lenticels*.—4 to 5 round lenticels per $cm^2$.

*Russet*.—Net-like; typically 10 to 25 percent of the fruit surface.

Fruit properties:

*Flesh color*.—Yellow (RHS 8C).

*Juice*.—Average.

*Firmness*.—Firm; 15.6 lb. at final harvest on Sep. 30, 2020 in Washington County, Md.

*Texture*.—Crunchy.

*Flavor*.—Pleasant with a richness of tastes.

*Soluble solids*.—13.6° Brix at final harvest on Sep. 30, 2020 in Washington County, Md.

*Aroma*.—Mild.

*Eating quality*.—Good.

*Keeping quality*.—Best before 4-5 months storage.

*Harvest date*.—Typically mid to late September; harvest maturity measurements were made on eating ripe fruit in Washington County, Md. on Sep. 30, 2020.

*Productivity of the fruit*.—Research planting on 'M.111' rootstock yielded about 2 bushels per tree at a spacing of 330 trees per acre; at 42 lbs. per bushel, the estimated yield would be 27,720 lbs. per acre.

*Core*.—4 to 5 cm in diameter depending on fruit size.

*Core lines*.—Heart-shaped; clasping.

*Carpellary area*.—Visible; 5 locules.

*Depth of calyx tube*.—6 mm.

*Seed cells*.—Generally 1-2 seeds per cell. Closed; 5 in number.

*Cell walls*.—Firm; translucent; Appears colorless.

Seeds:

*Number*.—Typically 10.

*Length*.—8.5 mm.

*Breadth*.—4 mm.

*Form*.—Pyriform.

*Color*.—Greyed-orange (RHS 166B).

*Plant/fruit disease and pest resistance/susceptibility*.—In addition to tree architecture which reduces pruning and training labor, 'MD-TAP1' trees have shown acceptable field tolerance to fireblight (*Erwinia amylovora*) and apple scab (*Venturia inequalis*) when grown in the Washington County, Md. and Queen Anne's County, Md. research orchards. These attributes coupled with its large fruit and annual production appear to make 'MD-TAP1' well suited for sustainable, organic, and home-grounds fruit plantings.

*Pollination*.—Diploid apples with an early-season bloom date. Compatibility with its 'Co-op 38' seed parent, has not been tested.

Use: For dessert.

What is claimed is:

1. A new and distinct apple variety named 'MD-TAP1' as shown and described herein.

* * * * *